United States Patent [19]
Malech

[11] 3,951,134
[45] Apr. 20, 1976

[54] APPARATUS AND METHOD FOR REMOTELY MONITORING AND ALTERING BRAIN WAVES

[75] Inventor: Robert G. Malech, Plainview, N.Y.

[73] Assignee: Dorne & Margolin Inc., Bohemia, N.Y.

[22] Filed: Aug. 5, 1974

[21] Appl. No.: 494,518

[52] U.S. Cl. ............................................ 128/2.1 B
[51] Int. Cl.² .......................................... A61B 5/04
[58] Field of Search ............... 128/1 C, 1 R, 2.1 B, 128/2.1 R, 419 R, 422 R, 420, 404, 2 R, 2 S, 2.05 R, 2.05 V, 2.05 F, 2.06 R; 340/248 A, 258 A, 258 B, 258 D, 229

[56] References Cited
UNITED STATES PATENTS

| | | | |
|---|---|---|---|
| 2,860,627 | 11/1958 | Harden et al. | 128/2.1 B |
| 3,096,768 | 7/1963 | Griffith, Jr. | 128/420 |
| 3,233,450 | 2/1966 | Fry | 128/2.1 R |
| 3,483,860 | 12/1969 | Namerow | 128/2.05 F |
| 3,495,596 | 2/1970 | Condict | 128/1 C |
| 3,555,529 | 1/1971 | Brown et al. | 128/2.1 R |
| 3,773,049 | 11/1973 | Rabichev et al. | 128/1 C |
| 3,796,208 | 3/1974 | Bloice | 128/2 S |

Primary Examiner—William E. Kamm
Attorney, Agent, or Firm—Darby & Darby

[57] ABSTRACT

Apparatus for and method of sensing brain waves at a position remote from a subject whereby electromagnetic signals of different frequencies are simultaneously transmitted to the brain of the subject in which the signals interfere with one another to yield a waveform which is modulated by the subject's brain waves. The interference waveform which is representative of the brain wave activity is re-transmitted by the brain to a receiver where it is demodulated and amplified. The demodulated waveform is then displayed for visual viewing and routed to a computer for further processing and analysis. The demodulated waveform also can be used to produce a compensating signal which is transmitted back to the brain to effect a desired change in electrical activity therein.

11 Claims, 2 Drawing Figures

APPARATUS AND METHOD FOR REMOTELY MONITORING AND ALTERING BRAIN WAVES

BACKGROUND OF THE INVENTION

Medical science has found brain waves to be a useful barometer of organic functions. Measurements of electrical activity in the brain have been instrumental in detecting physical and psychic disorder, measuring stress, determining sleep patterns, and monitoring body metabolism.

The present art for measurement of brain waves employs electroencephalographs including probes with sensors which are attached to the skull of the subject under study at points proximate to the regions of the brain being monitored. Electrical contact between the sensors and apparatus employed to process the detected brain waves is maintained by a plurality of wires extending from the sensors to the apparatus. The necessity for physically attaching the measuring apparatus to the subject imposes several limitations on the measurement process. The subject may experience discomfort, particulary if the measurements are to be made over extended periods of time. His bodily movements are restricted and he is generally confined to the immediate vicinity of the measuring apparatus. Furthermore, measurements cannot be made while the subject is conscious without his awareness. The comprehensiveness of the measurements is also limited since the finite number of probes employed to monitor local regions of brain wave activity do not permit observation of the total brain wave profile in a single test.

SUMMARY OF THE INVENTION

The present invention relates to apparatus and a method for monitoring brain waves wherein all components of the apparatus employed are remote from the test subject. More specifically, high frequency transmitters are operated to radiate electromagnetic energy of different frequencies through antennas which are capable of scanning the entire brain of the test subject or any desired region thereof. The signals of different frequencies penetrate the skull of the subject and impinge upon the brain where they mix to yield an interference wave modulated by radiations from the brain's natural electrical activity. The modulated interference wave is re-transmitted by the brain and received by an antenna at a remote station where it is demodulated, and processed to provide a profile of the suject's brain waves. In addition to passively monitoring his brain waves, the subject's neurological processes may be affected by transmitting to his brain, through a transmitter, compensating signals. The latter signals can be derived from the received and processed brain waves.

OBJECTS OF THE INVENTION

It is therefore an object of the invention to remotely monitor electrical activity in the entire brain or selected local regions thereof with a single measurement.

Another object is the monitoring of a subject's brain wave activity through transmission and reception of electromagnetic waves.

Still another object is to monitor brain wave activity from a position remote from the subject.

A further object is to provide a method and apparatus for affecting brain wave activity by transmitting electromagnetic signals thereto.

DESCRIPTION OF THE DRAWINGS

Other and further objects of the invention will appear from the following description and the accompanying drawings, which form part of the instant specification and which are to be read in conjunction therewith, and in which like reference numerals are used to indicate like parts in the various views.

DESCRIPTION OF THE PREFERRED EMBODIMENT

Figure 1:
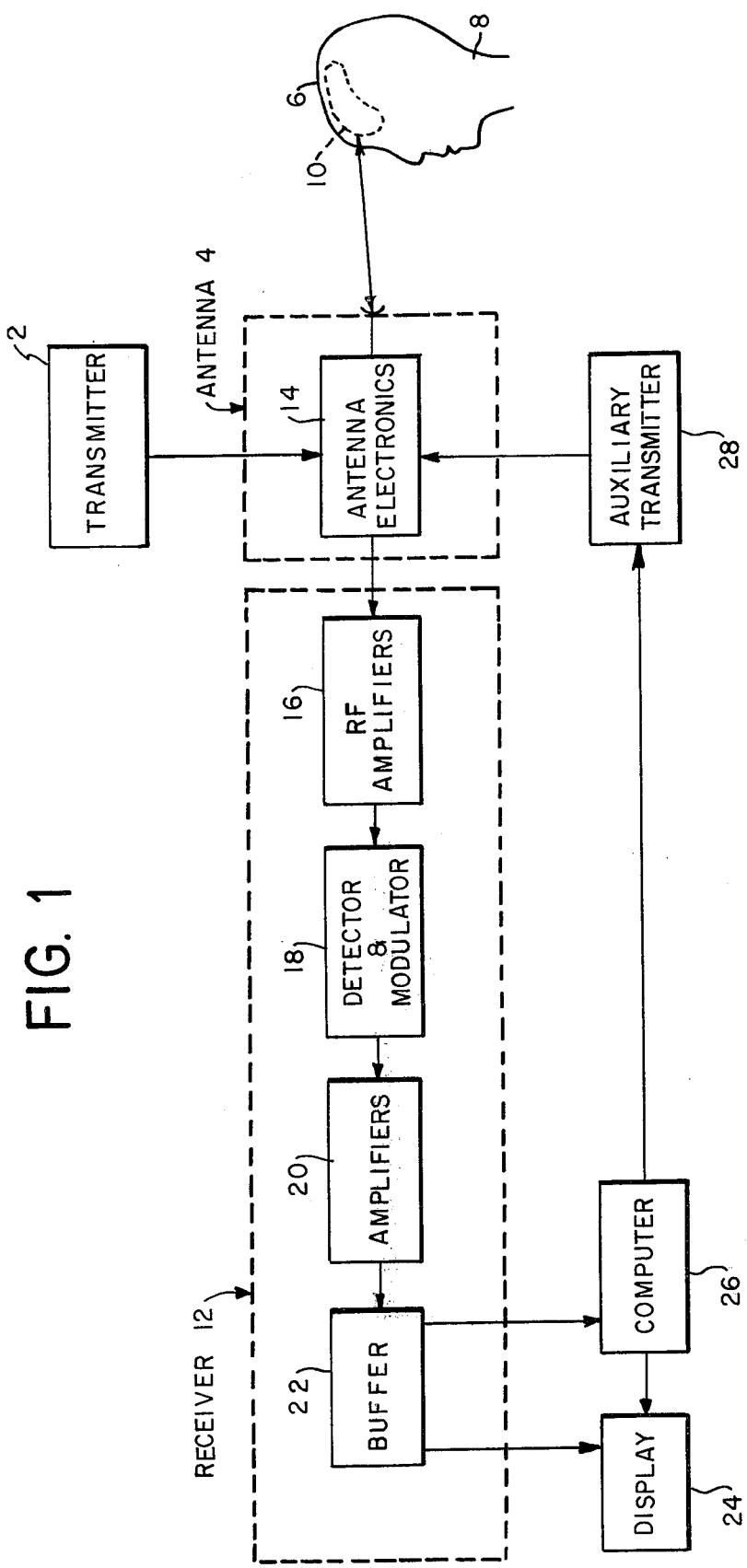
FIG. 1 is a block diagram showing the interconnection of the components of the apparatus of the invention.

Referring to the drawings, specifically FIG. 1, a high frequency transmitter 2 produces and supplies two electromagnetic wave signals through suitable coupling means 14 to an antenna 4. The signals are directed by the antenna 4 to the skull 6 of the subject 8 being examined. The two signals from the antenna 4, which travel independently, penetrate the skull 6 and impinge upon the tissue of the brain 10.

Within the tissue of the brain 10, the signals combine, much in the manner of a conventional mixing process technique, with each section of the brain having a different modulating action. The resulting waveform of the two signals has its greatest amplitude when the two signals are in phase and thus reinforcing one another. When the signals are exactly 180° out of phase the combination produces a resultant waveform of minimum amplitude. If the amplitudes of the two signals transmitted to the subject are maintained at identical levels, the resultant interference waveform, absent influences of external radiation, may be expected to assume zero intensity when maximum interference occurs, the number of such points being equal to the difference in frequencies of the incident signals. However, interference by radiation from electrical activity within the brain 10 causes the waveform resulting from interference of the two transmitted signals to vary from the expected result, i.e., the interference waveform is modulated by the brain waves. It is believed that this is due to the fact that brain waves produce electric charges each of which has a component of electromagnetic radiation associated with it. The electromagnetic radiation produced by the brain waves in turn reacts with the signals transmitted to the brain from the external source.

The modulated interference waveform is re-transmitted from the brain 10, back through the skull 6. A quantity of energy is re-transmitted sufficient to enable it to be picked up by the antenna 4. This can be controlled, within limits, by adjusting the absolute and relative intensities of the signals, originally transmitted to the brain. Of course, the level of the transmitted energy should be kept below that which may be harmful to the subject.

The antenna passes the received signal to a receiver 12 through the antenna electronics 14. Within the receiver the wave is amplified by conventional RF amplifiers 16 and demodulated by conventional detector and modulator electronics 18. The demodulated wave, representing the intra-brain electrical activity, is amplified by amplifiers 20 and the resulting information in electronic form is stored in buffer circuitry 22. From the buffers 22 the information is fed to a suitable visual display 24, for example one employing a cathode ray tube, light emitting diodes, liquid crystals, or a mechanical plotter. The information may also be channeled to a computer 26 for further processing and analysis with the output of the computer displayed by heretofore mentioned suitable means.

In addition to channeling its information to display devices 24, the computer 26 can also produce signals to control an auxiliary transmitter 28. Transmitter 28 is used to produce a compensating signal which is transmitted to the brain 10 of the subject 8 by the antenna 4. In a preferred embodiment of the invention, the compensating signal is derived as a function of the received brain wave signals, although it can be produced separately. The compensating signals affect electrical activity within the brain 10.

Figure 2:
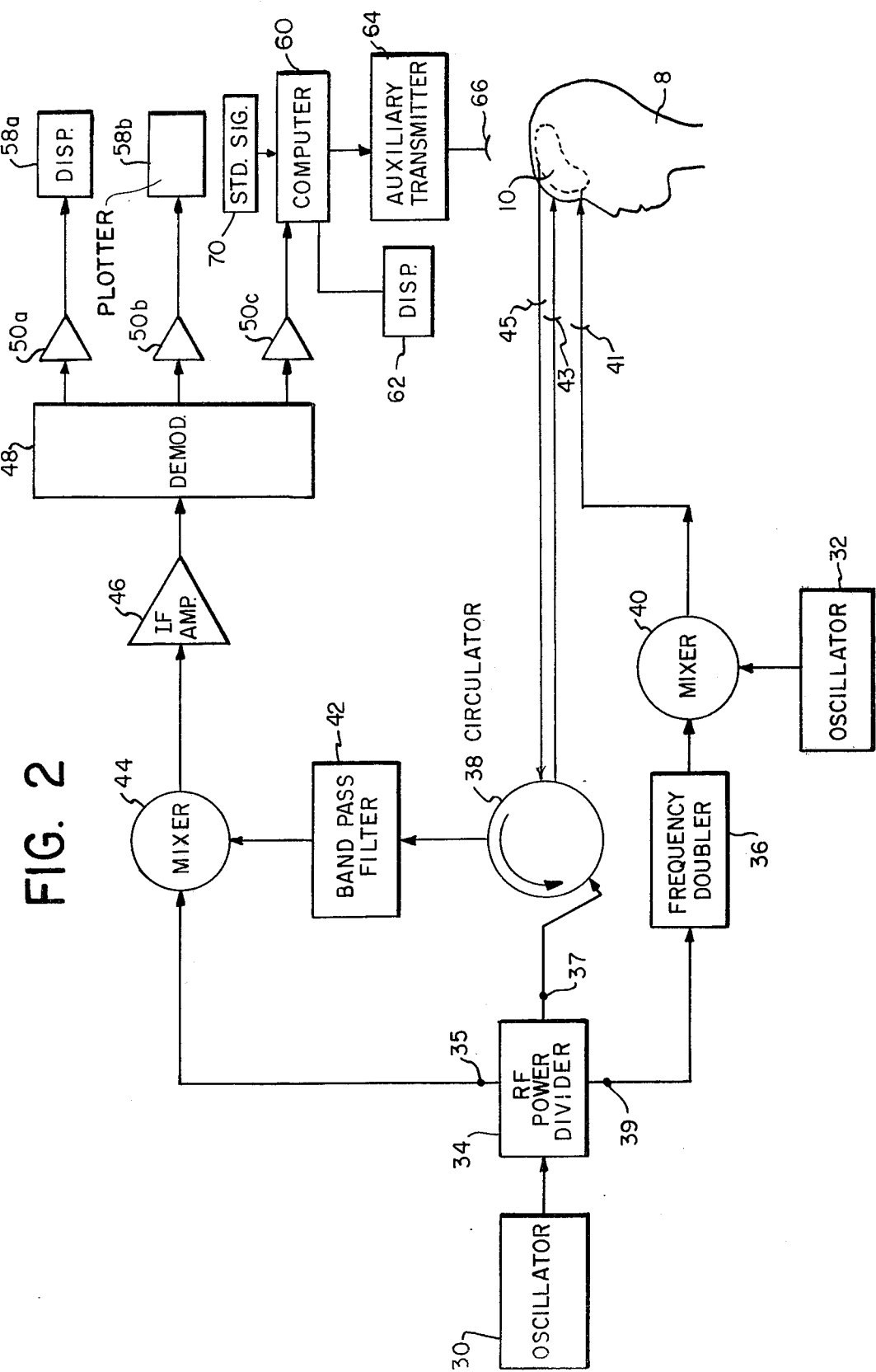
FIG. 2 is a block diagram showing signal flow in one embodiment of the apparatus.

Various configurations of suitable apparatus and electronic circuitry may be utilized to form the system generally shown in FIG. 1 and one of the many possible configurations is illustrated in FIG. 2. In the example shown therein, two signals, one of 100 MHz and the other of 210 MHz are transmitted simultaneously and combine in the brain 10 to form a resultant wave of frequency equal to the difference in frequencies of the incident signals, i.e., 110 MHz. The sum of the two incident frequencies is also available, but is discarded in subsequent filtering. The 100 MHz signal is obtained at the output 37 of an RF power divider 34 into which a 100 MHz signal generated by an oscillator 30 is injected. The oscillator 30 is of a conventional type employing either crystals for fixed frequency circuits or a tunable circuit set to oscillate at 100 MHz. It can be a pulse generator, square wave generator or sinusoidal wave generator. The RF power divider can be any conventional VHF, UHF or SHF frequency range device constructed to provide, at each of three outputs, a signal identical in frequency to that applied to its input.

The 210 MHz signal is derived from the same 100 MHz oscillator 30 and RF power divider 34 as the 100 MHz signal, operating in concert with a frequency doubler 36 and 10 MHz oscillator 32. The frequency doubler can be any conventional device which provides at its output a signal with frequency equal to twice the frequency of a signal applied at its input. The 10 MHz oscillator can also be of conventional type similar to the 100 MHz oscillator herebefore described. A 100 MHz signal from the output 39 of the RF power divider 34 is fed through the frequency doubler 36 and the resulting 200 MHz signal is applied to a mixer 40. The mixer 40 can be any conventional VHF, UHF or SHF frequency range device capable of accepting two input signals of differing frequencies and providing two output signals with frequencies equal to the sum and difference in frequencies respectively of the input signals. A 10 MHz signal from the oscillator 32 is also applied to the mixer 40. The 200 MHz signal from the doubler 36 and the 10 MHz signal from the oscillator 32 combine in the mixer 40 to form a signal with a frequency of 210 MHz equal to the sum of the frequencies of the 200 MHz and 10 MHz signals.

The 210 MHz signal is one of the signals transmitted to the brain 10 of the subject being monitored. In the arrangement shown in FIG. 2, an antenna 41 is used to transmit the 210 MHz signal and another antenna 43 is used to transmit the 100 MHz signal. Of course, a single antenna capable of operating at 100 MHz and 210 MHz frequencies may be used to transmit both signals. The scan angle, direction and rate may be controlled mechanically, e.g., by a reversing motor, or electronically, e.g., by energizing elements in the antenna in proper synchronization. Thus, the antenna(s) can be of either fixed or rotary conventional types.

A second 100 MHz signal derived from output terminal 37 of the three-way power divider 34 is applied to a circulator 38 and emerges therefrom with a desired phase shift. The circulator 38 can be of any conventional type wherein a signal applied to an input port emerges from an output port with an appropriate phase shift. The 100 MHz signal is then transmitted to the brain 10 of the subject being monitored via the antenna 43 as the second component of the dual signal transmission. The antenna 43 can be of conventional type similar to antenna 41 herebefore described. As previously noted, these two antennas may be combined in a single unit.

The transmitted 100 and 210 MHz signal components mix within the tissue in the brain 10 and interfere with one another yielding a signal of a frequency of 110 MHz, the difference in frequencies of the two incident components, modulated by electromagnetic emissions from the brain, i.e., the brain wave activity being monitored. This modulated 110 MHz signal is radiated into space.

The 110 MHz signal, modulated by brain wave activity, is picked up by an antenna 45 and channeled back through the circulator 38 where it undergoes an appropriate phase shift. The circulator 38 isolates the transmitted signals from the received signal. Any suitable diplexer or duplexer can be used. The antenna 45 can be of conventional type similar to antennas 41 and 43. It can be combined with them in a single unit or it can be separate. The received modulated 110 MHz signal is then applied to a band pass filter 42, to eliminate undesirable harmonics and extraneous noise, and the filtered 110 MHz signal is inserted into a mixer 44 into which has also been introduced a component of the 100 MHz signal from the source 30 distributed by the RF power divider 34. The filter 42 can be any conventional band pass filter. The mixer 44 may also be of conventional type similar to the mixer 40 herebefore described.

The 100 MHz and 110 MHz signals combine in the mixer 44 to yield a signal of frequency equal to the difference in frequencies of the two component signals, i.e., 10 MHz still modulated by the monitored brain wave activity. The 10 MHz signal is amplified in an IF amplifier 46 and channeled to a demodulator 48. The IF amplifier and demodulator 48 can both be of conventional types. The type of demodulator selected will depend on the characteristics of the signals transmitted to and received from the brain, and the information desired to be obtained. The brain may modulate the amplitude, frequency and/or phase of the interference waveform. Certain of these parameters will be more sensitive to corresponding brain wave characteristics than others. Selection of amplitude, frequency or phase demodulation means is governed by the choice of brain wave characteristic to be monitored. If desired, several different types of demodulators can be provided and used alternately or at the same time.

The demodulated signal which is representative of the monitored brain wave activity is passed through audio amplifiers 50 a, b, c which may be of conventional type where it is amplified and routed to displays 58 a, b, c and a computer 60. The displays 58 a, b, c present the raw brain wave signals from the amplifiers 50 a, b, c. The computer 60 processes the amplified brain wave signals to derive information suitable for viewing, e.g., by suppressing, compressing, or expanding elements thereof, or combining them with other information-bearing signals and presents that information on a display 62. The displays can be conventional ones such as the types herebefore mentioned employing electronic visual displays or mechanical plotters 58b. The computer can also be of conventional type, either analog or digital, or a hybrid.

A profile of the entire brain wave emission pattern may be monitored or select areas of the brain may be observed in a single measurement simply by altering the scan angle and direction of the antennas. There is no physical contact between the subject and the monitoring apparatus. The computer 60 also can determine a compensating waveform for transmission to the brain 10 to alter the natural brain waves in a desired fashion. The closed loop compensating system permits instantaneous and continuous modification of the brain wave response pattern.

In performing the brain wave pattern modification function, the computer 60 can be furnished with an external standard signal from a source 70 representative of brain wave activity associated with a desired nuerological response. The region of the brain responsible for the response is monitored and the received signal, indicative of the brain wave activity therein, is compared with the standard signal. The computer 60 is programmed to determine a compensating signal, responsive to the difference between the standard signal and received signal. The compensating signal, when transmitted to the monitored region of the brain, modulates the natural brain wave activity therein toward a reproduction of the standard signal, thereby changing the neurological response of the subject.

The computer 60 controls an auxiliary transmitter 64 which transmits the compensating signal to the brain 10 of the subject via an antenna 66. The transmitter 64 is of the high frequency type commonly used in radar applications. The antenna 66 can be similar to antennas 41, 43 and 45 and can be combined with them. Through these means, brain wave activity may be altered and deviations from a desired norm may be compensated. Brain waves may be monitored and control signals transmitted to the brain from a remote station.

It is to be noted that the configuration described is one of many possibilities which may be formulated without departing from the spirit of my invention. The transmitters can be monostratic or bistatic. They also can be single, dual, or multiple frequency devices. The transmitted signal can be continuous wave, pulse, FM, or any combination of these as well as other transmission forms. Typical operating frequencies for the transmitters range from 1 MHz to 40 GHz but may be altered to suit the particular function being monitored and the characteristics of the specific subject.

The individual components of the system for monitoring and controlling brain wave activity may be of conventional type commonly employed in radar systems.

Various subassemblies of the brain wave monitoring and control apparatus may be added, substituted or combined. Thus, separate antennas or a single multimode antenna may be used for transmission and reception. Additional displays and computers may be added to present and analyze select components of the monitored brain waves.

Modulation of the interference signal retransmitted by the brain may be of amplitude, frequency and/or phase. Appropriate demodulators may be used to decipher the subject's brain activity and select components of his brain waves may be analyzed by computer to determine his mental state and monitor his thought processes.

As will be appreciated by those familiar with the art, apparatus and method of the subject invention has numerous uses. Persons in critical positions such as drivers and pilots can be continuously monitored with provision for activation of an emergency device in the event of human failure. Seizures, sleepiness and dreaming can be detected. Bodily functions such as pulse rate, heartbeat reqularity and others also can be monitored and occurrences of hallucinations can be detected. The system also permits medical diagnoses of patients, inaccessible to physicians, from remote stations.

What is claimed is:

1. Brain wave monitoring apparatus comprising
    means for producing a base frequency signal,
    means for producing a first signal having a frequency related to that of the base frequency and at a predetermined phase related thereto,
    means for transmitting both said base frequency and said first signals to the brain of the subject being monitored,
    means for receiving a second signal transmitted by the brain of the subject being monitored in response to both said base frequency and said first signals,
    mixing means for producing from said base frequency signal and said received second signal a response signal having a frequency related to that of the base frequency, and
    means for interpreting said response signal.

2. Apparatus as in claim 1 where said receiving means comprises
    means for isolating the transmitted signals from the received second signals.

3. Apparatus as in claim 2 further comprising a band pass filter with an input connected to said isolating means and an output connected to said mixing means.

4. Apparatus as in claim 1 further comprising means for amplifying said response signal.

5. Apparatus as in claim 4 further comprising means for demodulating said amplified response signal.

6. Apparatus as in claim 5 further comprising interpreting means connected to the output of said demodulator means.

7. Apparatus according to claim 1 further comprising
    means for producing an electromagnetic wave control signal dependent on said response signal, and
    means for transmitting said control signal to the brain of said subject.

8. Apparatus as in claim 7 wherein said transmitting means comprises means for directing the electromagnetic wave control signal to a predetermined part of the brain.

9. A process for monitoring brain wave activity of a subject comprising the steps of
    transmitting at least two electromagnetic energy signals of different frequencies to the brain of the subject being monitored,
    receiving an electromagnetic energy signal resulting from the mixing of said two signals in the brain modulated by the brain wave activity and retransmitted by the brain in response to said transmitted energy signals, and, interpreting said received signal.

10. A process as in claim 9 further comprising the step of transmitting a further electromagnetic wave signal to the brain to vary the brain wave activity.

11. A process as in claim 10 wherein the step of transmitting the further signals comprises obtaining a standard signal, comparing said received electromagnetic energy signals with said standard signal, producing a compensating signal corresponding to the comparison between said received electrogagnetic energy signals and the standard signal, and transmitting the compensating signals to the brain of the subject being monitored.

\* \* \* \* \*